United States Patent
Bor et al.

(10) Patent No.: US 12,403,038 B2
(45) Date of Patent: Sep. 2, 2025

(54) SYSTEMS AND METHODS FOR CREATING A LENTICULE FOR PRESBYOPIA

(71) Applicant: Alcon Inc., Fribourg (CH)

(72) Inventors: Zsolt Bor, San Clemente, CA (US); Mario Klafke, Mainaschaff (DE); Johannes Krause, Nuremberg (DE); Keith Watanabe, Irvine, CA (US)

(73) Assignee: ALCON INC., Fribourg (CH)

( * ) Notice: Subject to any disclaimer, the term of this patent is extended or adjusted under 35 U.S.C. 154(b) by 788 days.

(21) Appl. No.: 17/643,440

(22) Filed: Dec. 9, 2021

(65) Prior Publication Data
US 2022/0183885 A1 Jun. 16, 2022

Related U.S. Application Data

(60) Provisional application No. 63/126,343, filed on Dec. 16, 2020.

(51) Int. Cl.
*A61F 9/008* (2006.01)

(52) U.S. Cl.
CPC ............... *A61F 9/00827* (2013.01); *A61F 2009/00872* (2013.01)

(58) Field of Classification Search
CPC .............. A61F 9/00827; A61F 9/00838; A61F 9/0084; A61F 2009/00872; A61F 2009/00882; A61F 2009/00895; A61F 2009/00897
USPC .......................................................... 606/4
See application file for complete search history.

(56) References Cited

U.S. PATENT DOCUMENTS

| | | | |
|---|---|---|---|
| 11,241,336 B2* | 2/2022 | Bischoff | A61F 9/013 |
| 11,564,838 B2* | 1/2023 | Fu | A61B 3/107 |
| 2010/0331831 A1 | 12/2010 | Bischoff | |
| 2015/0250652 A1 | 9/2015 | Holliday | |
| 2017/0143544 A1 | 5/2017 | Holliday | |
| 2017/0367883 A1* | 12/2017 | Malek Tabrizi | A61B 18/20 |
| 2019/0175281 A1 | 6/2019 | Dishler et al. | |
| 2019/0240003 A1 | 8/2019 | Klopotek | |
| 2021/0186759 A1* | 6/2021 | Sedky | A61F 9/00827 |
| 2021/0321869 A1 | 10/2021 | Bor | |
| 2021/0369105 A1 | 12/2021 | Bor | |
| 2022/0062034 A1* | 3/2022 | Abraham | A61F 9/00825 |

OTHER PUBLICATIONS

Juhasz, T. et al., "Corneal Refractive Surgery with Femtosecond Lasers", IEEE Journal of Selected Topics in Quantum Electornics, 1999, vol. 5, No. 4, 902-910.

* cited by examiner

*Primary Examiner* — Ahmed M Farah

(57) ABSTRACT

In certain embodiments, an ophthalmic surgical system for creating a lenticule in the cornea of an eye comprises controllable components (including a laser source and a scanner) and a computer. The laser source generates a laser beam, and the scanner directs the focal point of the laser beam. The computer determines a lenticule design for the lenticule having a posterior side and an anterior side. Either the posterior side or the anterior side has a central portion and a peripheral portion. The lenticule design is formed using a major lenslet and a minor lenslet, where the major lenslet is designed to correct to emmetropia. The lenticule design is formed by subtracting the minor lenslet from the major lenslet, where the subtraction of the minor lenslet yields the central portion. The computer instructs one or more of the controllable components to create the lenticule.

19 Claims, 6 Drawing Sheets

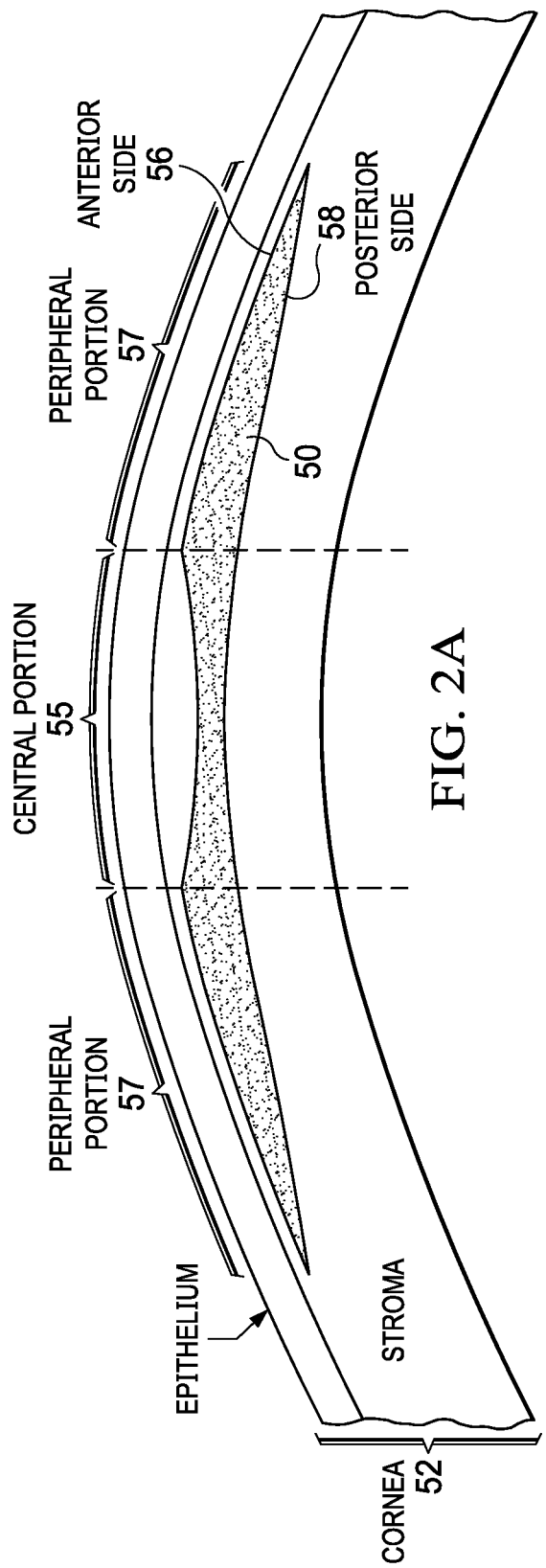
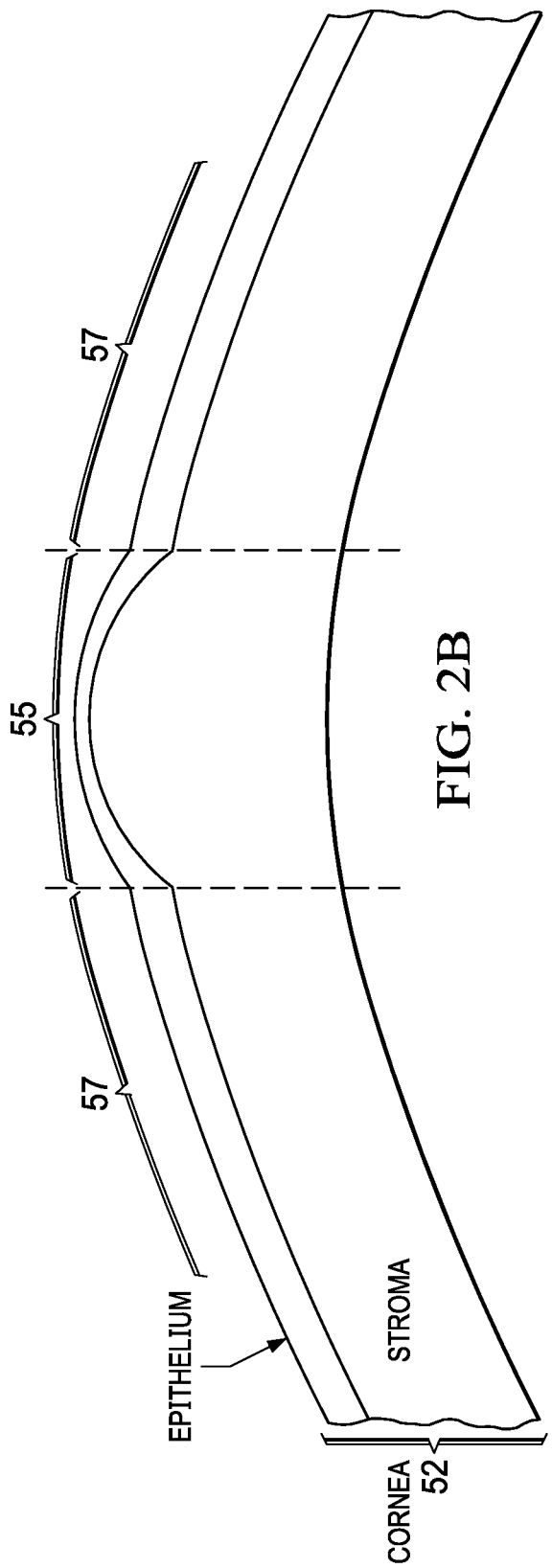

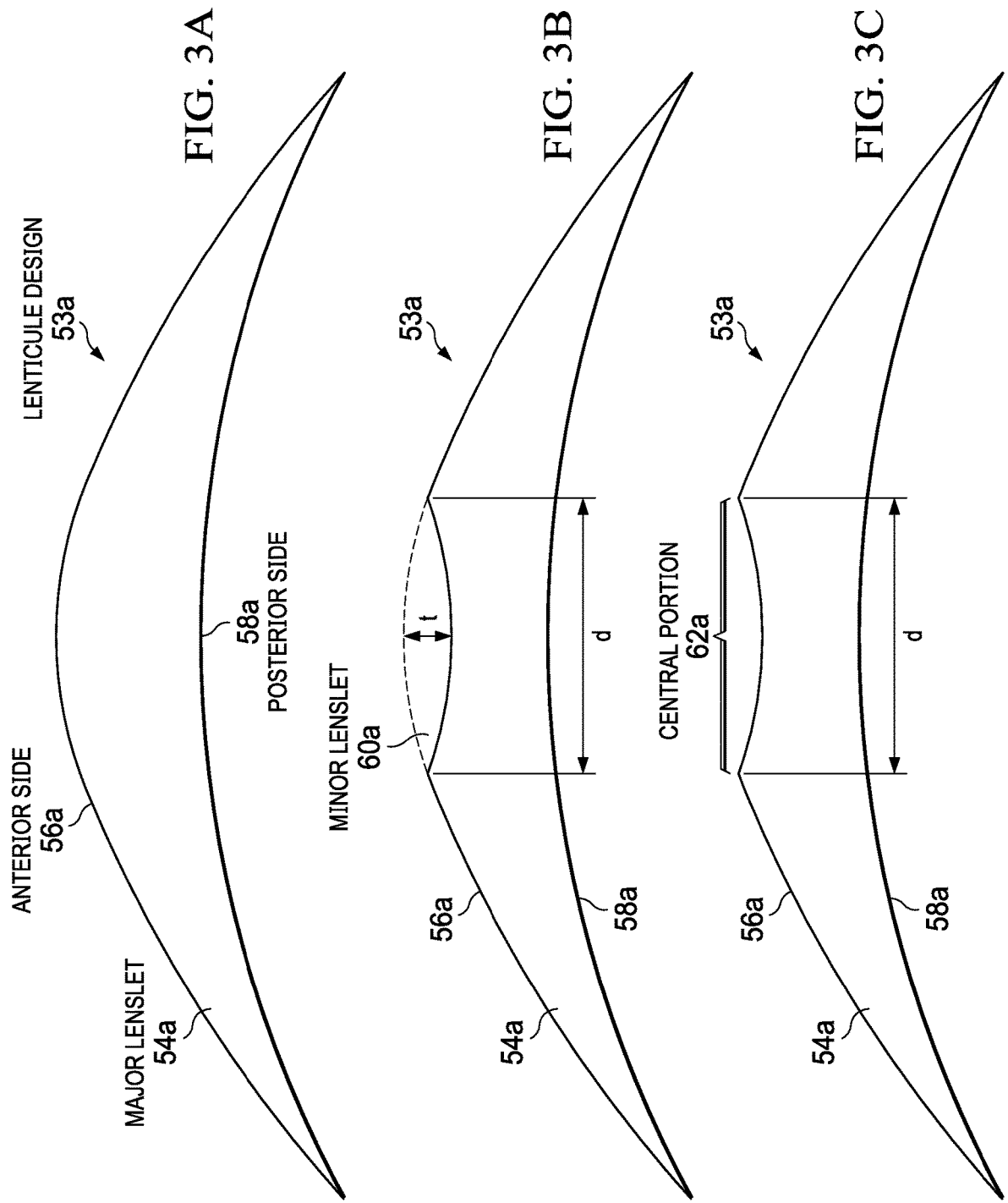

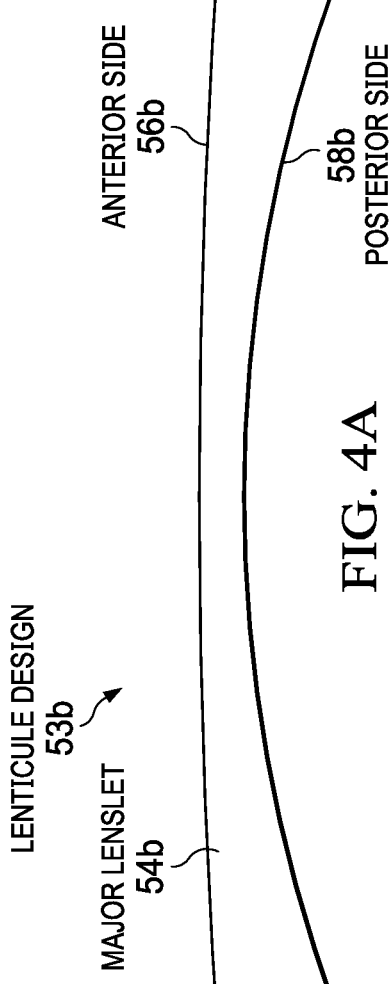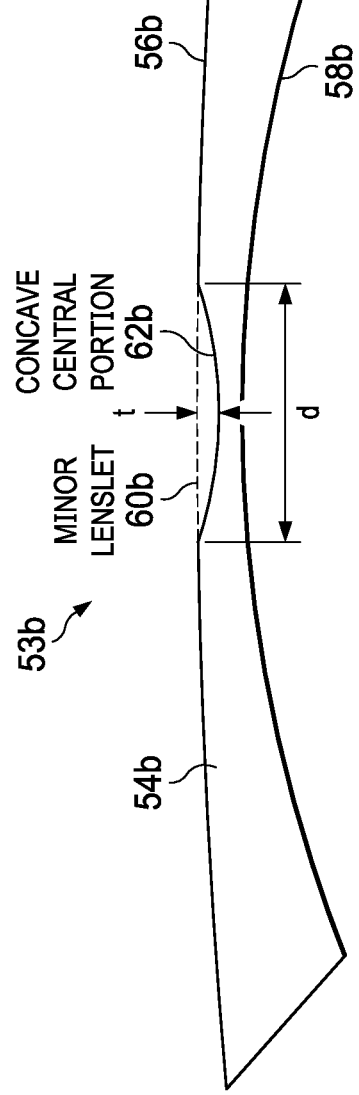

SYSTEMS AND METHODS FOR CREATING A LENTICULE FOR PRESBYOPIA

TECHNICAL FIELD

The present disclosure relates generally to ophthalmic surgical systems, and more particularly to ophthalmic surgical systems for creating a lenticule for presbyopia.

BACKGROUND

The lens of the eye changes shape to focus light onto the retina so you can see objects both near and far. When you are young, the lens is soft and flexible, easily changing shape. Presbyopia occurs typically after age 40, when the lens becomes more rigid and cannot change shape as easily. This causes the eye to focus light behind rather than onto the retina when looking at close objects, reducing near-vision ability.

There are approximately 1.7 billion presbyopic people worldwide, and approximately one-third of the population of the United States is presbyopic. Treatment for presbyopia includes lenses (e.g., glasses and contact lenses), implants (intraocular lenses (IOLs), scleral implants, and corneal inlays), and surgery (keratoplasty and refractive surgery). However, current treatments fail to provide satisfactory results in certain situations.

BRIEF SUMMARY

In certain embodiments, an ophthalmic surgical system for creating a lenticule in the cornea of an eye comprises controllable components (including a laser source and a scanner) and a computer. The laser source generates a laser beam having ultrashort pulses, where a propagation direction of the laser beam defines a z-axis. The scanner directs a focal point of the laser beam in an xy-plane orthogonal to the z-axis and in a z-direction parallel to the z-axis. The computer determines a lenticule design for the lenticule having a posterior side and an anterior side. Either the posterior side or the anterior side has a central portion and a peripheral portion. The lenticule design is formed using a major lenslet and a minor lenslet, where the major lenslet is designed to correct to emmetropia. The lenticule design is formed by subtracting the minor lenslet from the major lenslet, where the subtraction of the minor lenslet yields the central portion. The computer instructs one or more of the controllable components to perform the following to create the lenticule: create the posterior side of the lenticule according to the lenticule design; and create the anterior side of the lenticule according to the lenticule design.

Embodiments may include none, one, some, or all of the following features:

The central portion is spherically concave relative to a surface of the cornea.

The minor lenslet has a diameter of 1 to 4 millimeters.

The center of the minor lenslet has a thickness of 5 to 50 micrometers.

The major lenslet is designed to treat myopia, and the center of the major lenslet has a greater thickness than the periphery of the major lenslet.

The major lenslet is designed to treat hyperopia, the periphery of the major lenslet has a greater thickness than the center of the major lenslet.

The major lenslet comprises a parallel layer to accommodate removal of the minor lenslet. The parallel layer may accommodate removal of the minor lenslet and may yield a central buffer zone. The computer may determine a thickness of the parallel layer by: determining a thickest portion of the minor lenslet; determining a thickness of the major lenslet at the thickest portion of the minor lenslet; determining an additional thickness needed by the major lenslet to allow for removal of the minor lenslet; and calculating the thickness of the parallel layer according to the additional thickness. The computer may determine the additional thickness needed by the major lenslet to allow for removal of the minor lenslet and that yields a central buffer zone.

The computer is further configured to: generate a laser focal spot pattern corresponding to the lenticule design; and align the laser focal spot pattern relative to an xy position of a visual axis to create the lenticule.

The computer is further configured to: generate a laser focal spot pattern corresponding to the lenticule design, a point of the laser focal spot pattern representing a center of the central portion; determine an xy position of a visual axis of the eye; and align the point of the laser focal spot pattern relative to the xy position of the visual axis to create the lenticule.

In certain embodiments, a method for creating a lenticule in a cornea of an eye comprises: generating, by a laser source of one or more controllable components, a laser beam having a plurality of ultrashort pulses, a propagation direction of the laser beam defining a z-axis; directing, by a scanner of the one or more controllable components, a focal point of the laser beam in an xy-plane orthogonal to the z-axis and in a z-direction parallel to the z-axis; and determining, by a computer, a lenticule design for the lenticule having a posterior side and an anterior side, either the posterior side or the anterior side having a central portion and a peripheral portion, the lenticule design formed using a major lenslet and a minor lenslet, the major lenslet designed to correct to emmetropia, the lenticule design formed by subtracting the minor lenslet from the major lenslet, the subtraction of the minor lenslet yielding the central portion. The method further comprises instructing, by the computer, one or more of the controllable components to perform the following to create the lenticule: create the posterior side of the lenticule according to the lenticule design; and create the anterior side of the lenticule according to the lenticule design.

Embodiments may include none, one, some, or all of the following features:

The central portion is spherically concave relative to a surface of the cornea.

The minor lenslet has a diameter of 1 to 4 millimeters.

The center of the minor lenslet has a thickness of 5 to 50 micrometers.

The major lenslet comprises a parallel layer to accommodate removal of the minor lenslet.

The method further comprises: generating, by the computer, a laser focal spot pattern corresponding to the lenticule design; and aligning, by the computer, the laser focal spot pattern relative to an xy position of a visual axis to create the lenticule.

The method further comprises: generating a laser focal spot pattern corresponding to the lenticule design, a point of the laser focal spot pattern representing a center of the central portion; determining an xy position of a visual axis of the eye; and aligning the point of the laser focal spot pattern relative to the xy position of the visual axis to create the lenticule.

In certain embodiments, an ophthalmic surgical system for creating a lenticule in the cornea of an eye comprises controllable components (including a laser source and a scanner) and a computer. The laser source generates a laser beam having ultrashort pulses, where a propagation direction of the laser beam defines a z-axis. The scanner directs the focal point of the laser beam in an xy-plane orthogonal to the z-axis and in a z-direction parallel to the z-axis. The computer determines a lenticule design for the lenticule having a posterior side and an anterior side. Either the posterior side or the anterior side has a central portion and a peripheral portion. The lenticule design is formed using a major lenslet and a minor lenslet, where the major lenslet is designed to correct to emmetropia. The major lenslet comprises a parallel layer to accommodate removal of the minor lenslet and to yield a central buffer zone. The minor lenslet has a diameter of 1 to 4 millimeters, and the center of the minor lenslet has a thickness of 5 to 50 micrometers. The lenticule design is formed by subtracting the minor lenslet from the major lenslet, where the subtraction of the minor lenslet yields the central portion that is spherically concave relative to a surface of the cornea. The computer generates a laser focal spot pattern corresponding to the lenticule design, determines an xy position of a visual axis of the eye, and aligns the laser focal spot pattern relative to the xy position of the visual axis. The computer instructs one or more of the controllable components to perform the following to create the lenticule: create the posterior side of the lenticule according to the lenticule design; and create the anterior side of the lenticule according to the lenticule design.

BRIEF DESCRIPTION OF THE DRAWINGS

FIGS. 2A and 2B illustrate an example of a lenticule that may be created by the system of FIG. 1;

FIGS. 3A, 3B, and 3C illustrate an example of a lenticule design that the system of FIG. 1 may use to create a lenticule for myopic presbyopia correction;

FIGS. 4A and 4B illustrate an example of a lenticule design that the system of FIG. 1 may use to create a lenticule for hyperopic presbyopia correction;

DESCRIPTION OF EXAMPLE EMBODIMENTS

Figure 1:
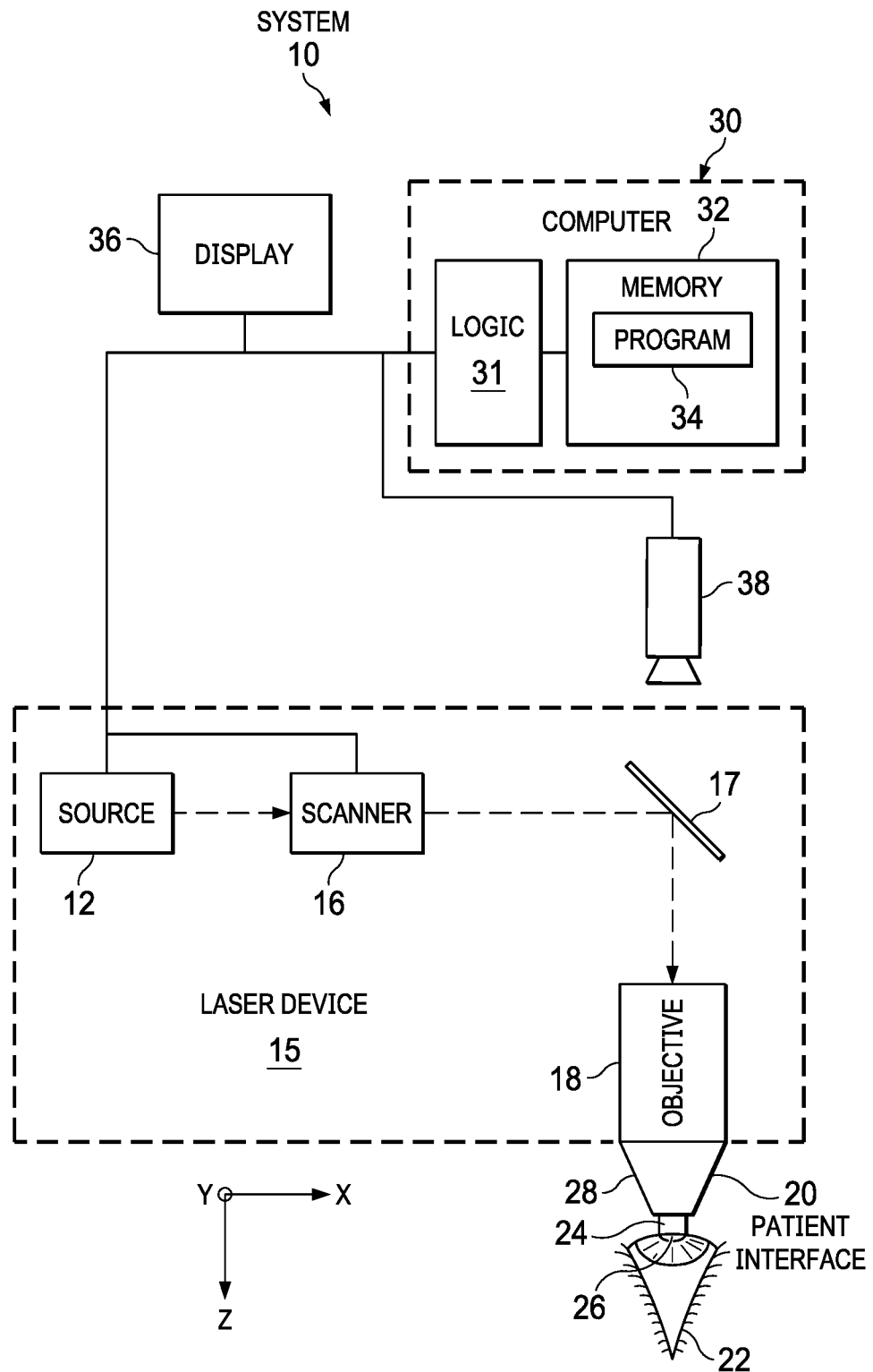
FIG. 1 illustrates an example of an ophthalmic surgical system configured to create a lenticule in a cornea to treat presbyopia, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

In general, an ophthalmic surgical system creates a lenticule in the cornea of an eye. The lenticule has a central portion designed for near vision and a peripheral portion for far vision. The lenticule is removed from the cornea to reshape the cornea. The central part of the resulting cornea provides for near vision and the peripheral part provides for far vision.

FIG. 1 illustrates an example of an ophthalmic surgical system 10 configured to create a lenticule that treats presbyopia in the cornea of an eye 22, according to certain embodiments. In the embodiments, a computer of system 10 determines a lenticule design for the lenticule, where the posterior and/or anterior side of the lenticule has a central portion and a peripheral portion. The lenticule design is formed by subtracting a minor lenslet from a major lenslet. The major lenslet is designed to correct to emmetropia. Removal of the minor lenslet yields a concave central portion that provides near-vision correction. The computer instructs one or more controllable components of system 10 to create the lenticule according to the lenticule design.

In the illustrated example, system 10 includes a laser device 15, a patient interface 20, a camera 38, and a control computer 30, coupled as shown. Laser device 15 includes controllable components, such as a laser source 12, a scanner 16, one or more optical elements 17, and/or a focusing objective 18, controllable by a computer such as computer 30, coupled as shown. Computer 30 includes logic 31, a memory 32 (which stores a computer program 34), and a display 36, coupled as shown. Patient interface 20 includes a contact portion 24 (with an abutment face 26) and a sleeve 28 coupled as shown.

According to an example of an overview of operation, laser source 12 generates a laser beam having ultrashort pulses, where a propagation direction of the laser beam defines a z-axis and/or z-direction. Scanner 16 directs a focal point of the laser beam in an xy-plane that is orthogonal to the z-axis. Objective 18 focuses the focal point towards the cornea of eye 22. Computer 30 determines a lenticule design for a lenticule using a major lenslet and a minor lenslet. Computer 30 also instructs one or more controllable components of system 10 to create the lenticule according to the lenticule design.

Turning to the parts of system 10, laser source 12 generates a laser beam with ultrashort pulses. An ultrashort pulse refers to a light pulse that has a duration of less than a nanosecond, such as on the order of picoseconds, femtoseconds, or attoseconds. The laser beam may have any suitable wavelength, such as a wavelength in the range of 300 to 1500 nanometers (nm), e.g., a wavelength in the range of 300 to 650, 650 to 1050, 1050 to 1250, and/or 1250 to 1500 nm, such as 340 to 350 nm, e.g., 345 nm±1 nm. The focal point of the laser beam may create a laser-induced optical breakdown (LIOB) in tissue (e.g., the cornea) to yield a photodisruption in the tissue. The laser beam may be precisely focused to yield precise photodisruptions, which may reduce or avoid unnecessary destruction of other tissue.

Scanner 16 longitudinally and transversely directs the focal point of the laser beam. The longitudinal direction refers to the direction of the laser beam propagation, i.e., the z-direction. Scanner 16 may longitudinally direct the laser beam in any suitable manner. For example, scanner 16 may include a longitudinally adjustable lens, a lens of variable refractive power, or a deformable mirror that can control the z-position of the focal point. The transverse direction refers to directions orthogonal to the direction of beam propagation, i.e., the x- and y-directions. Scanner 16 may transversely direct the laser beam in any suitable manner. For example, scanner 16 may include a pair of galvanometrically-actuated scanner mirrors that can be tilted about mutually perpendicular axes. As another example, scanner 16 may include an electro-optical crystal that can electro-optically steer the laser beam.

One (or more) optical elements 17 direct the laser beam towards focusing objective 18. An optical element 17 can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, optical element 17 is a mirror. Focusing objective 18 focuses the focal point of laser beam through the patient interface 20 towards a point of eye 22. In the example, focusing objective 18 is an objective lens, e.g., an f-theta objective.

Patient interface 20 interfaces with the cornea of eye 22 to couple eye 22 to laser device 15. In the example, patient interface 20 has sleeve 28 coupled to contact portion 24. Sleeve 28 detachably couples to focusing objective 18. Contact portion 24 may be translucent or transparent to the laser beam and has an abutment face 26 that interfaces with the cornea. Abutment face 26 may have any suitable shape, e.g., planar, convex, or concave.

Camera 38 records images of the movement of eye 22, which includes movement of the marker created in eye 22. Examples of camera 38 include a video, optical coherence tomography (OCT), or eye-tracking camera. Camera 38 delivers image data, which represent recorded images of the eye 22, to computer 30. Computer 30 may use the image data to, e.g., facilitate creation of the lenticule.

Computer 30 determines a lenticule design for a lenticule. In some embodiments, computer 30 may determine the lenticule design by determining major and minor lenslets and subtracting the minor lenslet from the major lenslet. In these embodiments, computer 30 determines a lenticule design for the lenticule having a posterior side and an anterior side. The anterior side and/or the posterior side has a central portion and a peripheral portion. The lenticule design is formed using a major lenslet and a minor lenslet. The major lenslet is designed to correct to emmetropia. The lenticule design is formed by subtracting the minor lenslet from the major lenslet. The computer also instructs one or more controllable components of system 10 to perform the following to create the lenticule: create the posterior side of the lenticule according to the lenticule design; and create the anterior side of the lenticule according to the lenticule design.

In other embodiments, computer 30 may determine the lenticule design by retrieving the design from memory 32, where the design was determined from the major and minor lenslets as described above.

In some embodiments, computer 30 generates a laser focal spot pattern corresponding to the lenticule design and/or aligns the spot pattern relative to an axis of the eye (e.g., optical or visual axis) to create the lenticule. Computer 30 may generate a 3-dimensional spot pattern by calculating the surfaces corresponding to the lenticule described by the lenticule design, and then determining the laser spots that yield the surfaces. In certain cases, a particular point of the laser focal spot pattern represents the center of the central portion. Computer 30 may align the spot pattern relative to an axis of the eye by receiving a measurement or coordinates (e.g., xy coordinates) identifying the location of the axis, and then aligning the spot pattern at the axis. In certain embodiments, computer 30 may determine the xy position of the visual axis according to methods described in U.S. Patent Application Nos. 63/010,293 (filed 15 Apr. 2020) and 63/033,327 (filed 2 Jun. 2020). In certain cases, computer 30 may align the particular point representing the center of the central portion with the xy position of the visual axis.

Computer 30 controls controllable components (e.g., laser source 12, scanner 16, optical elements 17, and/or focusing objective 18) in accordance with instructions (which may be stored in computer program 34) to photodisrupt corneal tissue to create the lenticule. In some embodiments, computer 30 instructs the controllable components of system 10 to create the posterior side of the lenticule according to the lenticule design and create the anterior side of the lenticule according to the lenticule design.

FIGS. 2A and 2B illustrate an example of a lenticule 50 that may be created by system 10 of FIG. 1. FIG. 2A shows lenticule 50 created in a cornea 52, and FIG. 2B shows cornea 52 after removal of lenticule 50. Lenticule 50 has an anterior side 56 and a posterior side 58. Anterior side 56 and/or posterior side 58 may have a central portion 55 and a peripheral portion 57. Central portion 55 is substantially centered about the center of lenticule 50, and peripheral portion 57 extends from central portion 55 to the edge of lenticule 50. In certain embodiments, central portion 55 provides near-vision correction, and peripheral portion 57 provides far-vision correction.

Lenticule 50 is thinner at the center, so removal of lenticule 50 yields a protrusion at central portion 55. After removal, the epithelium may become thinner above central portion 55. This thinning of the epithelium is called "epithelial compensation". Epithelial compensation is an inherent property of the epithelium that helps smooth out the anterior surface of the cornea to maintain good optical quality. The thinning of the epithelium generally reduces the height of the central protrusion, but does not eliminate it.

The design of central portion 55 is determined by removing a minor lenslet from a major lenslet. In certain embodiments, removal of the minor lenslet yields a central portion 55 that is concave relative to the corneal surface, and may be spherically concave. The concave central portion 55 provides for near-vision correction in the central portion of the visual field of eye 22.

Major and minor lenslets may have any suitable size and/or shape, and computer 30 may determine the dimensions of major and minor lenslets in any suitable manner. In certain embodiments, computer 30 may receive information describing the refractive correction, and determine the dimensions from the information. In the embodiments, computer 30 may calculate the dimensions of the major lenslet from information describing far-vision correction. In certain examples, the diameter of the major lenslet is 4 to 11 millimeters (e.g., 6 to 9 millimeters), and the pre-surgical depth of posterior side 58 is 90 to 300 micrometers. In certain examples, a thickness of 14 to 18 micrometers corresponds to approximately 1 diopter of correction, e.g., 14 to 18 micrometers corresponds to a correction of −1 diopter, 30 to 36 micrometers corresponds to a correction of −2 diopters, etc. The location of the thickness (e.g., center or periphery of the lenticule) depends on whether the correction is for myopia or hyperopia, are described in FIGS. 3A through 5D.

In certain embodiments, the major lenslet may be designed to correct myopia or hyperopia to emmetropia. Emmetropia is the state of vision in which a faraway object at infinity is in sharp focus with the eye lens in a neutral or relaxed state. Emmetropia may be in the range of +1 to −1 diopters. Examples of major lenslets for myopia and hyperopia correction are described in FIGS. 3A through 5D.

In the embodiments, computer 30 may calculate the dimensions of the minor lenslet from information describing near-vision correction. In certain examples, the diameter of the minor lenslet is 1 to 4 millimeters (e.g., 1 to 2, 2 to 3, and/or 3 to 4 millimeters), and the center of the minor lenslet has a thickness of 5 to 50 micrometers (e.g., 5 to 10, 10 to 20, 20 to 30, 30 to 40, and/or 40 to 50 micrometers). Generally, a minor lenslet with a greater central thickness provides greater presbyopic correction. In an example, a minor lenslet with a spherical shape, a diameter of 2 millimeters, and a central thickness of 30 micrometers adds a power of 2.5 to 4.0 diopters.

FIGS. 3A to 3C illustrate an example of a lenticule design 53 (53a) that system 10 of FIG. 1 may use to create lenticule 50 for myopic presbyopia correction. FIG. 3A shows a major lenslet 54 (54a), which forms the body of lenticule 50. In the illustrated example, major lenslet 54a corrects myopia. Accordingly, the anterior side 56a of major lenslet 54a has a greater curvature than the posterior side 58a of major lenslet 54a such that the center of major lenslet 54a is thicker than the periphery. In certain examples, a thickness of 14 to 18 micrometers at the center corresponds to approximately 1 diopter of correction.

FIG. 3B shows a minor lenslet 60 (60a), which is removed from major lenslet 52 to yield the final lenticule design 53. In the illustrated example, the diameter d of the minor lenslet is 1 to 4 millimeters, and the center of the minor lenslet has a thickness t of 5 to 50 micrometers. FIG. 3C shows the final lenticule design 53a after removal of minor lenslet 60a from major lenslet 52a, which yields a concave central portion 62a (i.e., concave relative to the corneal surface).

FIGS. 4A and 4B illustrate an example of a lenticule design 53 (53b) that system 10 of FIG. 1 may use to create lenticule 50 for hyperopic presbyopia correction. In the illustrated example, major lenslet 54b corrects hyperopia. Accordingly, the posterior side 58b of major lenslet 54b has a greater curvature than the anterior side 56b of major lenslet 54b. such that the periphery of major lenslet 54a is thicker than the center. "Periphery" may encompass the edge of major lenslet 54b as well as the region proximate to the edge, e.g., within 5 millimeters of the edge. In certain examples, a thickness difference of 14 to 18 micrometers between the center and the edge of the periphery corresponds to approximately 1 diopter of correction.

FIG. 4B shows a minor lenslet 60 (60b), which is removed from major lenslet 52b to yield the final lenticule design 53b. Removal of minor lenslet 60b from major lenslet 52b, yields a concave central portion 62b (i.e., concave relative to the corneal surface).

Figure 5A:
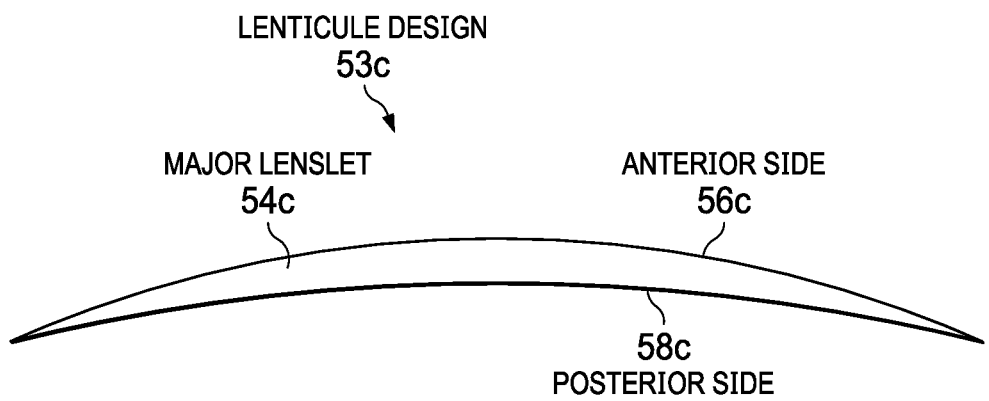
FIGS. 5A, 5B, 5C, and 5D illustrate an example of a lenticule design that the system of FIG. 1 may use to create a lenticule for low-diopter myopic presbyopia correction.
Figure 5B:
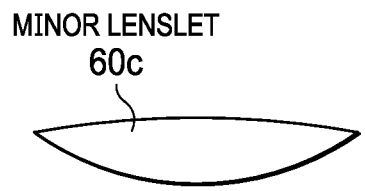

FIGS. 5A through 5D illustrate an example of a lenticule design 53 (53c) that system 10 of FIG. 1 may use to create lenticule 50 for low-diopter myopic presbyopia correction. FIGS. 5A and 5B show a major lenslet 54c for a low-diopter correction, e.g., less than −3 diopter, and minor lenslet 60c to be removed. Low-diopter major lenslet 54c may be very thin, even at the center of lenslet 54c. In some cases, the center of a low-diopter major lenslet 54c may be thinner than the thickness t of minor lenslet 60c to be removed or may not allow for a sufficient remaining buffer zone after removal. A buffer zone may be a region of sufficient thickness (e.g., greater than 5 or 10 micrometers) that allows for, e.g., removal of lenticule 50 without tearing lenticule 50. A central buffer zone may be a buffer zone located in the central area of lenticule 50.

Figure 5C:
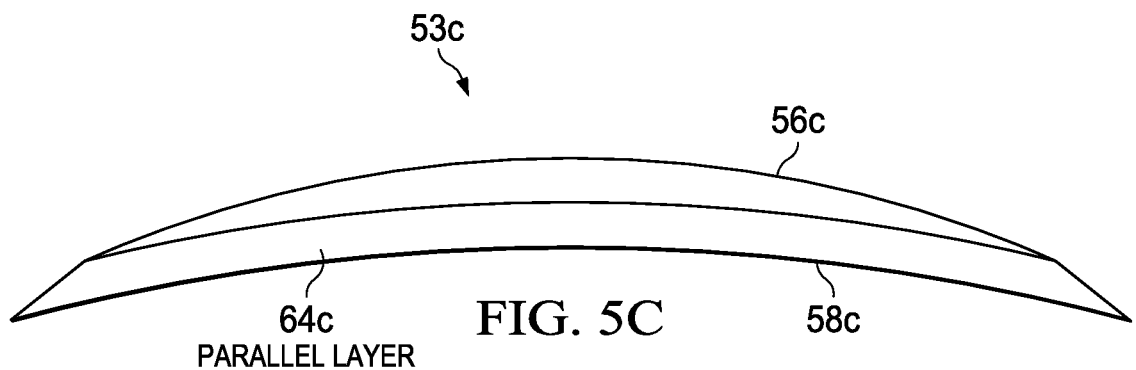

FIG. 5C shows a parallel layer 64c added to the posterior side 58c of low-diopter major lenslet 54c. Parallel layer 64c is a layer of substantially uniform thickness that provides thickness and optionally a buffer zone to allow for efficient removal of minor lenslet 60c, and has substantially no refractive power. In certain embodiments, anterior and posterior sides of parallel layer 64c may be parallel. In the embodiments, the thickness of parallel layer 64c may be determined by: (1) determining the thickest portion of minor lenslet 60c; (2) determining the thickness of major lenslet 54c at this portion; (3) calculating the additional thickness needed by major lenslet 54c to allow for removal of minor lenslet that yields an optional buffer zone of at least, e.g., 5 or 10 micrometers.

Figure 5D:
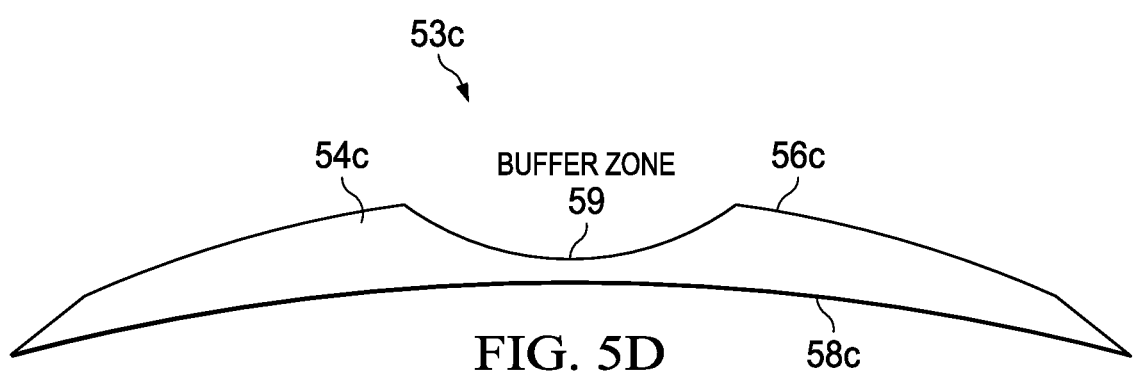

FIG. 5D shows the final lenticule design 53c after parallel layer 64c is added to major lenslet 54c, and minor lenslet 60c is removed from major lenslet 54c. Parallel layer 64c allows for removal of minor lenslet 60c, while leaving a remaining buffer zone 59.

Figure 6:
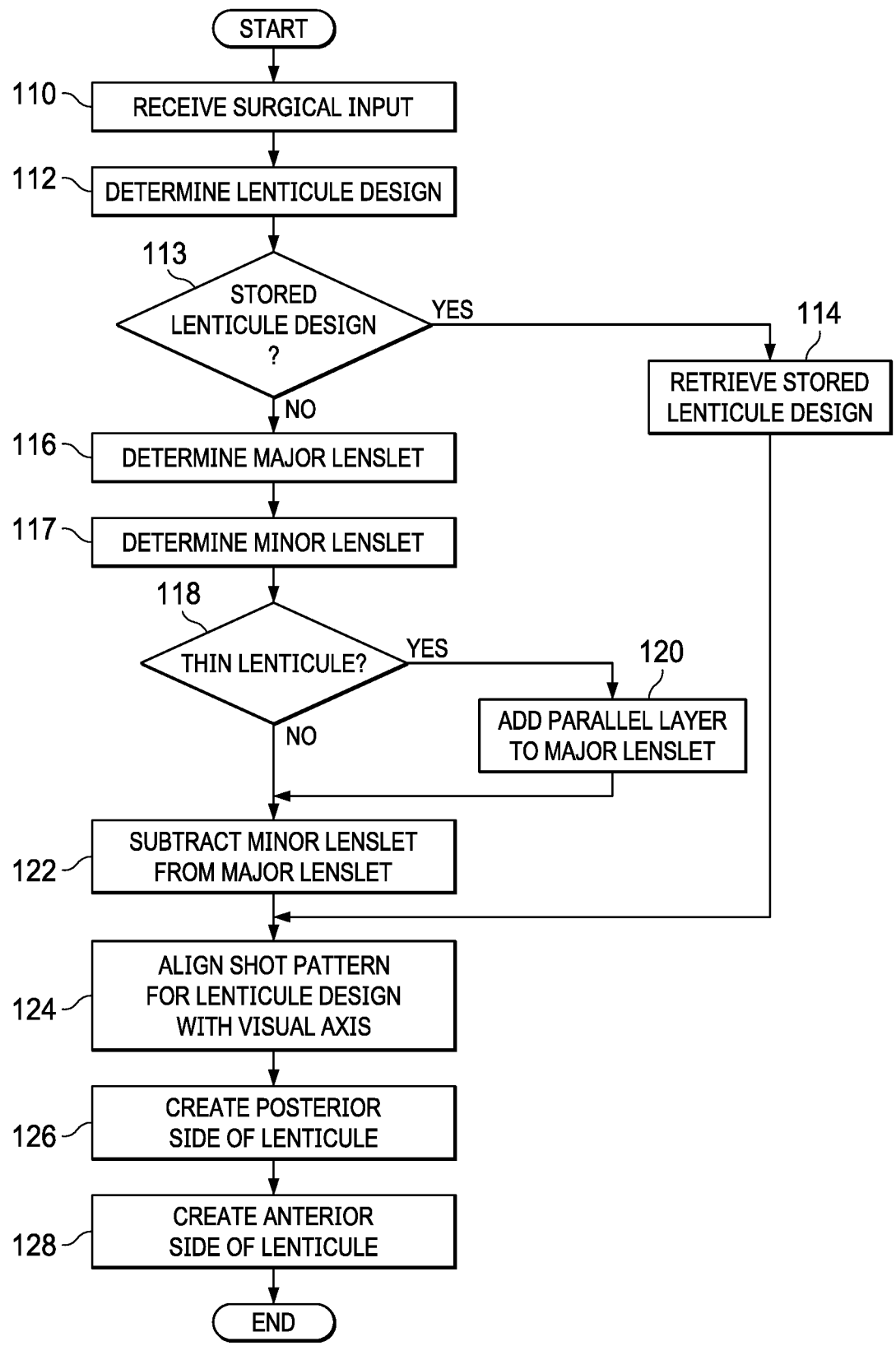
FIG. 6 illustrates a method for creating a lenticule in a cornea that may be performed by the system of FIG. 1, according to certain embodiments.

FIG. 6 illustrates a method for creating a lenticule in a cornea of an eye that may be performed by system 10 of FIG. 1, according to certain embodiments. The method starts at step 110, where computer 30 receives surgical input describing a surgical procedure for creating the lenticule. The surgical input may include information that computer 30 can use to retrieve or to calculate a lenticule design that describes the lenticule. The surgical input may describe the patient's eye, e.g., the spherical error, cylinder error, axis of the cylinder error, added power (spherical error for reading distance correction), and/or xy position of the visual axis.

Computer 30 determines the lenticule design from the surgical input at step 112. The lenticule design may be stored at step 113, or may need to be calculated. If the lenticule design is stored at step 113, the method proceeds to step 114, where computer 30 retrieves the stored lenticule design. Then the method proceeds to step 126, where computer 30 begins creating the lenticule.

If there is no stored lenticule design at step 113, the method proceeds to steps 116 to 124, where computer 30 calculates the lenticule design. Computer 30 determines the major lenslet at step 116. In certain cases, the major lenslet may be designed to treat myopia, and the anterior side of the major lenslet has a greater curvature than the posterior side of the major lenslet. In other cases, the major lenslet may be designed to treat hyperopia, and the posterior side of the major lenslet has a greater curvature than the anterior side of the major lenslet. Computer 30 determines the minor lenslet at step 117. The minor lenslet may have any suitable shape and/or size. In certain examples, the diameter of the minor lenslet is 1 to 4 millimeters, and the center of the minor lenslet has a thickness of 5 to 50 micrometers.

The major lenslet may yield a thin lenticule at step 118 that cannot accommodate removal of a minor lenslet and yield a remaining buffer zone. If the major lenslet yields a thin lenticule at step 118, the method proceeds to step 120, where computer 30 adds a parallel layer to the major lenslet, and then proceeds to step 124. If the major lenslet does not yield a thin lenticule at step 118, the method proceeds directly to step 124. Computer 30 subtracts the minor lenslet from the major lenslet to determine the lenticule design at step 124.

At step 126, computer 30 aligns the xy position of the spot pattern for the lenticule design with the visual axis of the eye. In certain embodiments, computer 30 may determine the spot pattern by calculating the surfaces corresponding to the lenticule described by the lenticule design, and then determining coordinates of the laser spots that yield the surfaces. In certain embodiments, computer 30 may align the spot pattern relative to an axis of the eye (e.g., optical or visual) by receiving a measurement or coordinates identifying the location of the axis and then aligning the spot pattern with the axis.

Computer 30 instructs controllable components to create the posterior side of the lenticule at step 128. Computer 30 instructs controllable components to create the anterior side of the lenticule at step 130. The method then ends.

A component (such as the control computer) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface (e.g., a Graphical User Interface (GUI)) is a type of interface that a user can utilize to interact with a computer. Examples of user interfaces include a display, touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by the electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic surgical system for creating a lenticule in a cornea of an eye, comprising:
a plurality of controllable components comprising:
a laser source configured to generate a laser beam having a plurality of ultrashort pulses, a propagation direction of the laser beam defining a z-axis; and
a scanner configured to direct a focal point of the laser beam in an xy-plane orthogonal to the z-axis and in a z-direction parallel to the z-axis;
a computer configured to:
determine a lenticule design for the lenticule having a posterior side and an anterior side, either the posterior side or the anterior side having a central portion and a peripheral portion, the lenticule design formed using a major lenslet and a minor lenslet, the major lenslet designed to correct to emmetropia, the lenticule design formed by subtracting the minor lenslet from the major lenslet, the subtraction of the minor lenslet yielding the central portion; and
instruct one or more of the controllable components to perform the following to create the lenticule:
create the posterior side of the lenticule according to the lenticule design; and
create the anterior side of the lenticule according to the lenticule design.

2. The ophthalmic surgical system of claim 1, wherein the central portion is spherically concave relative to a surface of the cornea.

3. The ophthalmic surgical system of claim 1, wherein the minor lenslet has a diameter of 1 to 4 millimeters.

4. The ophthalmic surgical system of claim 1, wherein the center of the minor lenslet has a thickness of 5 to 50 micrometers.

5. The ophthalmic surgical system of claim 1, wherein the major lenslet is designed to treat myopia, a center of the major lenslet having a greater thickness than a periphery of the major lenslet.

6. The ophthalmic surgical system of claim 1, wherein the major lenslet is designed to treat hyperopia, a periphery of the major lenslet having a greater thickness than a center of the major lenslet.

7. The ophthalmic surgical system of claim 1, wherein the major lenslet comprises a parallel layer to accommodate removal of the minor lenslet.

8. The ophthalmic surgical system of claim 7, wherein the parallel layer accommodates removal of the minor lenslet and yields a central buffer zone.

9. The ophthalmic surgical system of claim 7, the computer configured to determine a thickness of the parallel layer by:
determining a thickest portion of the minor lenslet;
determining a thickness of the major lenslet at the thickest portion of the minor lenslet;
determining an additional thickness needed by the major lenslet to allow for removal of the minor lenslet; and
calculating the thickness of the parallel layer according to the additional thickness.

10. The ophthalmic surgical system of claim 9, wherein determining an additional thickness needed by the major lenslet to allow for removal of the minor lenslet further comprises:
determining the additional thickness needed by the major lenslet to allow for removal of the minor lenslet and that yields a central buffer zone.

11. The ophthalmic surgical system of claim 1, the computer further configured to:
generate a laser focal spot pattern corresponding to the lenticule design; and
align the laser focal spot pattern relative to an xy position of a visual axis to create the lenticule.

12. The ophthalmic surgical system of claim 1, the computer further configured to:
generate a laser focal spot pattern corresponding to the lenticule design, a point of the laser focal spot pattern representing a center of the central portion;
determine an xy position of a visual axis of the eye; and
align the point of the laser focal spot pattern relative to the xy position of the visual axis to create the lenticule.

13. A method for creating a lenticule in a cornea of an eye, comprising:
generating, by a laser source of one or more controllable components, a laser beam having a plurality of ultra-short pulses, a propagation direction of the laser beam defining a z-axis;
directing, by a scanner of the one or more controllable components, a focal point of the laser beam in an xy-plane orthogonal to the z-axis and in a z-direction parallel to the z-axis;
determining, by a computer, a lenticule design for the lenticule having a posterior side and an anterior side, either the posterior side or the anterior side having a central portion and a peripheral portion, the lenticule design formed using a major lenslet and a minor lenslet, the major lenslet designed to correct to emmetropia, the lenticule design formed by subtracting the minor lenslet from the major lenslet, the subtraction of the minor lenslet yielding the central portion; and
instructing, by the computer, one or more of the controllable components to perform the following to create the lenticule:
create the posterior side of the lenticule according to the lenticule design; and
create the anterior side of the lenticule according to the lenticule design.

14. The method of claim 13, wherein the central portion is spherically concave relative to a surface of the cornea.

15. The method of claim 13, wherein the minor lenslet has a diameter of 1 to 4 millimeters.

16. The method of claim 13, wherein the center of the minor lenslet has a thickness of 5 to 50 micrometers.

17. The method of claim 13, wherein the major lenslet comprises a parallel layer to accommodate removal of the minor lenslet.

18. The method of claim 13, further comprising:
generating, by the computer, a laser focal spot pattern corresponding to the lenticule design; and
aligning, by the computer, the laser focal spot pattern relative to an xy position of a visual axis to create the lenticule.

19. The method of claim 13, further comprising:
generating a laser focal spot pattern corresponding to the lenticule design, a point of the laser focal spot pattern representing a center of the central portion;
determining an xy position of a visual axis of the eye; and
aligning the point of the laser focal spot pattern relative to the xy position of the visual axis to create the lenticule.

* * * * *